United States Patent [19]

Amano et al.

[11] 4,169,889

[45] Oct. 2, 1979

[54] ANTIBIOTIC BN-200 SUBSTANCE AND PROCESS FOR PRODUCTION THEREOF

[75] Inventors: Shoichi Amano, Kawasaki; Shinji Miyadoh, Yokohama; Mitsugu Itoh, Machida; Norio Ezaki, Yokohama; Eiichi Akita, Kamakura; Yujiro Yamada, Yokohama, all of Japan

[73] Assignee: Meiji' Seika Kaisha, Ltd., Tokyo, Japan

[21] Appl. No.: 948,459

[22] Filed: Oct. 4, 1978

[30] Foreign Application Priority Data

Oct. 4, 1977 [JP] Japan .............................. 52-118538

[51] Int. Cl.$^2$ ........................................... A61K 35/00

[52] U.S. Cl. ................................. 424/122; 435/128; 435/847

[58] Field of Search ........................ 424/122; 195/80

[56] References Cited

U.S. PATENT DOCUMENTS

| 3,769,403 | 10/1973 | Hara et al. ........................ 424/122 |
| 3,819,835 | 6/1974 | Hasegawa et al. ................ 424/122 |

Primary Examiner—Jerome D. Goldberg
Attorney, Agent, or Firm—Sughrue, Rothwell, Mion, Zinn and Macpeak

[57] ABSTRACT

An antibiotic BN-200 substance produced by cultivating a BN-200 substance strain of the genus Erwinia and a process for producing the BN-200 substance.

2 Claims, 2 Drawing Figures

ANTIBIOTIC BN-200 SUBSTANCE AND PROCESS FOR PRODUCTION THEREOF

BACKGROUND OF THE INVENTION

This invention relates to an antibiotic, and a process for its production. More specifically, this invention relates to a novel antibiotic BN-200 substance and to a process for producing the antibiotic BN-200 substance which comprises cultivating a BN-200 substance-producing strain of the genus Erwinia in the culture medium, and separating and recovering the BN-200 substance from the culture broth.

SUMMARY OF THE INVENTION

It has now been found that a substance which shows a strong action against Gram-positive and Gram-negative bacteria is produced in the cultivation product of a strain of the genus Erwinia, and isolated the active substance in pure form from the cultivation product. Examination of the characteristics of the substance has confirmed that the substance is a novel antibiotic different from known antibiotics. This effective substance has therefore been named BN-200 substance.

Accordingly, this invention in one embodiment provides an antibiotic BN-200 substance, having the physical and chemical characteristics hereinafter described.

In another embodiment of this invention, this invention provides a process for producing the antibiotic BN-200 substance which comprises aerobically cultivating a BN-200 substance-producing strain of the genus Erwinia in a culture medium containing assimilable carbon and nitrogen sources at a temperature of about 20° C. to about 35° C. and recovering the BN-200 substance from the culture broth.

DETAILED DESCRIPTION OF THE INVENTION

Figure 1:
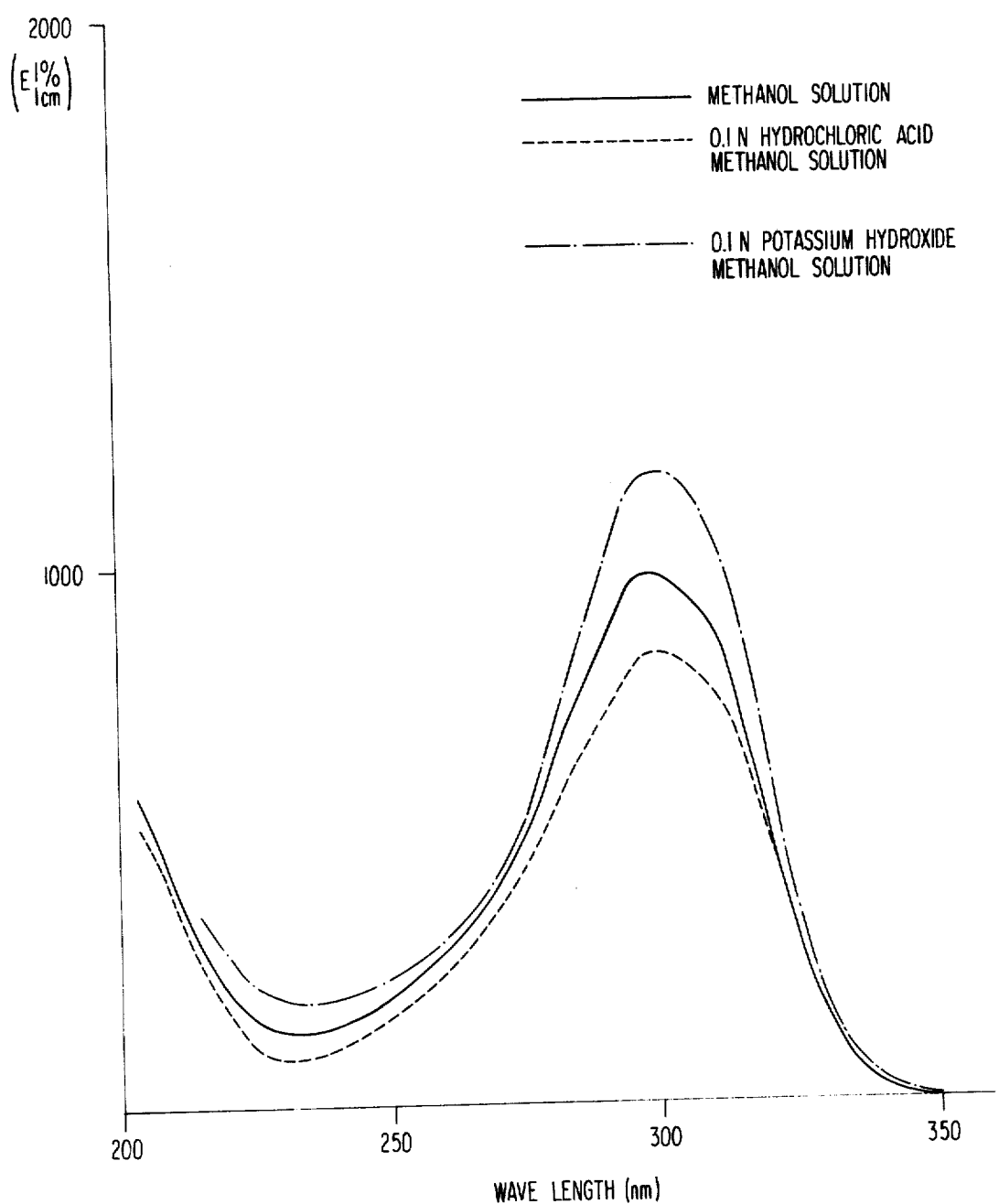
FIG. 1 is the ultraviolet absorption spectrum of the BN-200 substance as determined in methanol.

One example of the strain of the genus Erwinia used in this invention is Erwinia sp. BN-200 newly isolated by the present inventors from a putrefied plant in Hyogo Prefecture, Japan. This strain has been deposited with the Fermentation Research Institute, Agency of Industrial Science and Technology, Ministry of International Trade and Industry of Japan under the accession number FERM-P No. 3561 and deposited in the American Type Culture Collection (ATCC) under the accession number 31420.

The microbiological characteristics of Erwinia sp. BN-200 are as follows.

(a) Morphological Characteristics

Cells cultivated on bouillon agar medium are rod shaped having a size of 0.5–0.7×0.8–1.5 micron, with peritrichial movement. No spore or sporangiophore is formed, nor is polymorphism exhibited. Gram stain and acid fastness are both negative.

(b) Culture Characteristics (1) Bouillon Agar Culture: The bacterial cells are yellow brown, and yellowness increases as cultivation proceeds. The colonies show a marked crease-like growth, and do not show viscousness or motility. No formation of a diffusible pigment is noted.

(2) Bouillon Culture: The entire culture medium becomes turbid.

(3) Bouillon Gelatin Stab Culture: Liquefied (4) Litmus Milk Culture: Peptonization proceeds with weak alkalinity exhibited.

(c) Physiological Characteristics (1) Reduction of Nitrate: negative
(2) Denitration Reaction: negative
(3) MR (methyl red) Test: positive
(4) VP (Voges-Proskauer) Test: negative
(5) Production of Indole: positive
(6) Production of Hydrogen Sulfide: negative
(7) Hydrolysis of Starch: positive
(8) Utilization of Citric Acid: positive
(9) Utilization of Inorganic Nitrogen Sources: Ammonium salts are the sole inorganic nitrogen source utilizable.
(10) Production of Pigments: The cells become yellow, but no water-soluble pigment is produced.
(11) Urease: negative
(12) Oxidase: negative
(13) Growth Temperature: 10 to 35° C., but no growth at 42° C.
(14) Facultatively anaerobic
(15) OF Test (Heuleifson's method): F type; no gas is produced.
(16) Ornithine Decarboxylation Reaction: negative
(17) Lysine Decarboxylation Reaction: negative
(18) KCN Resistance: resistance exhibited
(19) Utilization of Malonic Acid: negative
(20) Utilization of Sugars: Utilizes glucose, maltose, xylose, mannitol, lactose and saccharose.

The BN-200 strain having the above bacteriological characteristics was compared with strains listed in *Bergey's Manual of Determinative Bacteriology*, 8th edition, 1974, and the following conclusions were drawn.

The BN200 strain belongs to the family Enterobacteriaceae in view of the fact that the BN-200 strain is a Gramnegative rod-shaped bacterium with motility, is facultatively anaerobic and oxidase negative, and does not form a gas. The BN-200 strain has been identified as belonging to the genus Erwinia in view of the utilization of sugar, negative nitrate reduction, KCN resistance, and negative ornithine and lysine decarboxylation reactions.

Variants of the Erwinia sp. BN-200 strain can be produced by artificial means using ultraviolet light, X-rays, high-frequency waves, radiation, chemicals, etc. All variants of the genus Erwinia so produced can be used in this invention so long as they have the ability to produce the BN-200 substance.

Various culture media used in ordinary microbial fermentation processes can be used to cultivate BN-200 substance-producing strains and to produce and accumulate the BN-200 substance. Glucose, glycerol, sucrose, dextrin, starch, and millet jelly, for example, can be used as carbon sources. Nitrogen sources that can be used include, for example, peptone, meat extract, bouillon powder, corn steep liquor, soybean cake, fish meal, ammonium sulfate, and ammonium chloride. Inorganic salts such as sodium chloride, potassium chloride, and calcium carbonate are additionally used whenever required. If desired, an anti-foamer can be added.

The cultivation can be suitably conducted using a liquid culture medium, such as a shake-culture method, or a submerged aeration agitation culture method. The cultivation temperature is optimal in the range of about 20 to about 35° C., and a suitable cultivation time ranges from 6 to 24 hours.

Recovery of the BN-200 substance from the culture broth can be performed by considering the physical and chemical properties of the BN-200 substance described hereinafter.

The following procedure was used in assaying the BN-200 substance. A mixture of 2% of mycin assay agar (a product of Kyoei Seiyaku K.K.) and 0.5% of bacto-agar (a product of DIFCO) was used as an assay medium. *Bacillus subtilis* ATCC 6633 strain was used as an assaying bacterium.

With the above assay method, a linear relationship is exhibited between the logarithm of the concentration of the BN-200 substance (pure product) and the diameter of the zone of inhibition when the concentration of the BN-200 substance is in the range of 31 mcg/ml to 100 mcg/ml, with the inhibition zone diameter ranging from 22.5 mm to 30.3 mm (paper disc method).

The BN-200 substance can be extracted and purified according to its physical and chemical properties described below. The method shown below is efficient. That is, the fermentation broth containing the active ingredient is filtered to remove solid matter. The filtrate is adsorbed on an adsorbent such as Diaion HP-10, Diaion HP-20 and Diaion HP-30 (tradenames, produced by Mitsubishi Chemical Industries, Ltd., Japan), Amberlite XAD-2 (a tradename, produced by Rohm & Haas Co., U.S.A.), and the active substance is eluted with alkaline 70% aqueous methanol solution (pH: 8 - 9). The methanol is distilled off, and the residue is extracted with, e.g., ethyl acetate, benzene, chloroform, n-butanol, methyl isobutyl ketone, etc. to obtain crude BN-200 substance. The crude product is then purified by a suitable combination of a countercurrent distribution method, a precipitation method, and a gel-filtration chromatographic method using Sephadex LH-20 (a tradename, produced by Pharmacia Co., Sweden), etc. to obtain purified BN-200 substance.

When the resulting powder product is chromatographed on a thin layer of silica gel using various solvent systems, e.g., chloroform-methanol, benzene-ethanol, benzene acetone, etc., a single spot is formed in all systems used. This shows that the resulting powder product is BN-200 substance in pure form.

The BN-200 substance has the following physical and chemical properties.

(1) Elemental Analysis: C 67.46%, H 7.24%, N 7.55%, O 17.75 % (balance)

(2) Molecular Weight: 520; determined from the titration value.

(3) Melting Point: Begins to turn brown at 150° C., and begins to decompose at 156° C.

(4) Specific Rotatory Power: $[\alpha]_D^{20} = -70.7$ (C=1, methanol).

(5) Ultraviolet Absorption Spectrum: Shown in FIG. 1. The absorption maximum is 298 nm ($E_{1cm}^{1\%}$ 980) in a methanol solution, 298 nm ($E_{1\ cm}^{1\%}$ 840) in a 0.1 N hydrochloric acid methanol solution, and 300 nm ($E_{1\ cm}^{1\%}$ 1180) in a 0.1 N potassium hydroxide methanol solution.

Figure 2:
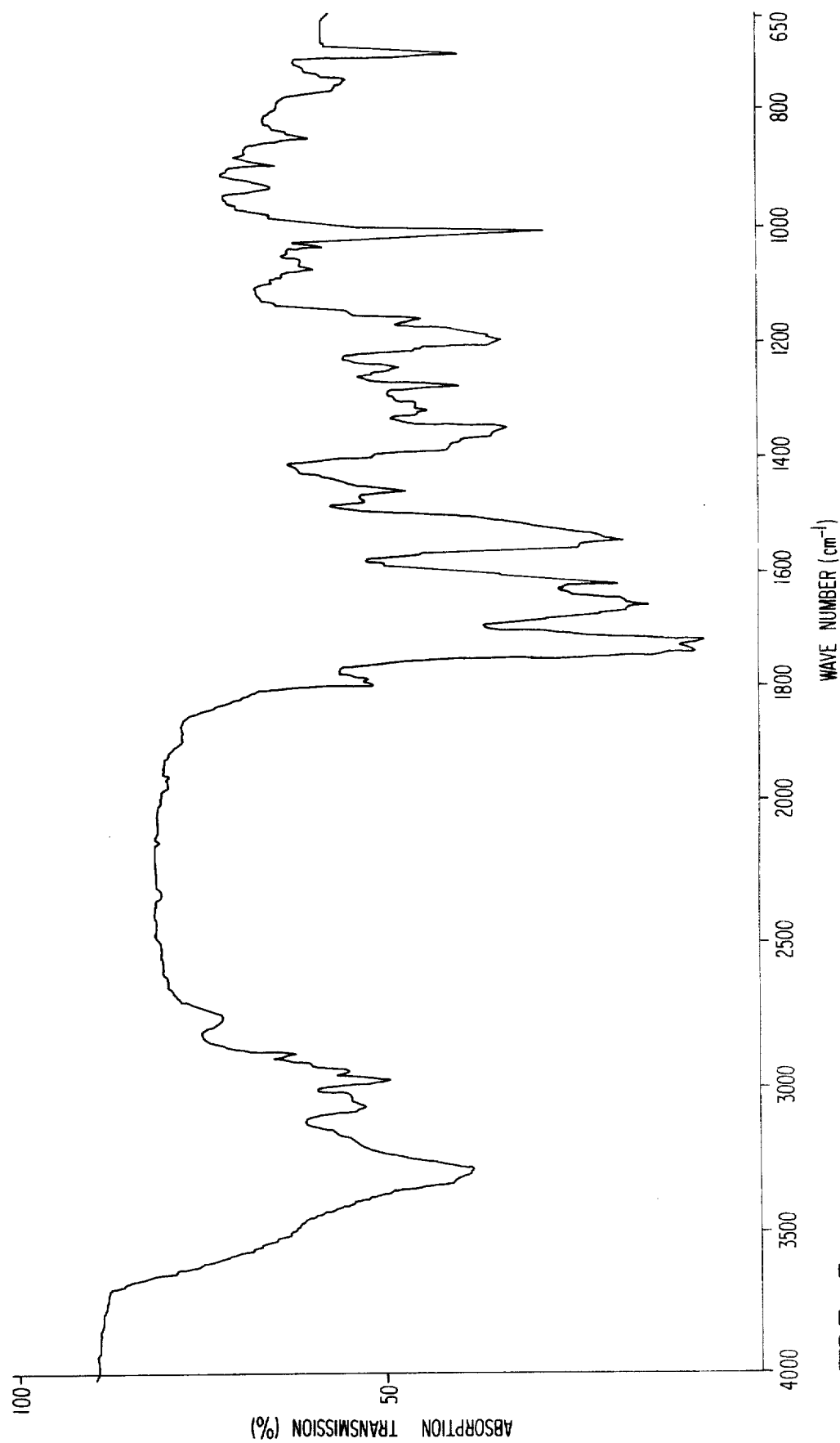
FIG. 2 is the infrared absorption spectrum of the BN-200 substance using the KBr tablet method.

(6) Infrared Absorption Spectrum: The spectrum measured using the potassium bromide tablet method is shown in FIG. 2.

(7) Solubility in Solvents: Soluble in methanol, ethanol, pyridine, dimethylformamide, acetone, and dimethyl sulfoxide, and insoluble in benzene, ethyl acetate, chloroform, carbon tetrachloride, petroleum ether, and water.

(8) Color Reactions: Positive with ferric chloride, potassium permanganate, and iodine, and negative with ninhydrin, Sakaguchi, biuret, Fehling, Molisch, and anthrone.

(9) Form and Color: white powder

(10) Rf Values in Silica Gel Thin-Layer Chromatography:
Chloroform-Methanol (9:1)—0.57
Benzene-Ethanol (9:1)—0.47
Benzene-Acetone (1:1)—0.76

The antimicrobial activities of the BN-substance against various microorganisms were measured and the minimum growth inhibitory concentrations (MIC) of BN-200 substance against various microorganisms are shown in Table 1 below.

Table 1

Minimum Growth Inhibitory Concentrations (liquid dilution method)

| Microorganism Tested | Minimum Growth Inhibitory Concentration (mcg/ml) | Culture Medium |
|---|---|---|
| *Bacillus subtilis* (ATCC 6633) | 0.7 | 1 |
| *Bacillus stearothermophilis* | 0.7 | 1 |
| *Bacillus subtilis* (UV-34) | 3.2 | 1 |
| *Staphylococcus aureus* 209P | 1.5 | 1 |
| *Staphylococcus aureus* 52-34, tetracycline - and erythromycin-resistant | 1.5 | 1 |
| *Sarcina lutea* | >100 | 1 |
| *Escherichia coli* NIHJ | 6.5 | 1 |
| *Escherichia coli* $K_{12}R$ | 6.5 | 1 |
| *Pseudomonas aeruginosa* | 100 | 1 |
| *Klebsiella pneumoniae* | 100 | 1 |
| *Proteus vulgaris* | 0.3 | 1 |
| *Microbacterium smegmatis*, Kanamycin-resistant | >100 | 2 |
| *Microbacterium smegmatis*, Streptomycin-resistant | >100 | 2 |
| *Candida albicans* | 100 | 3 |

Note: Culture Medium
1 is a bouillon medium
2 is a glycerol-bouillon medium
3 is a glucose-peptone medium From the results shown in Table 1 above, it is apparent that BN-200 substance can be used as medicines for humans and for veterinary applications.

The acute toxicity of BN-200 substance was determined by intraperitoneal administration to mice, and the mice were observed for a week. All mice survived at a dose of 100 mg/kg.

The BN-200 substance of this invention can be administered at a dose of about 20 to about 300 mg/kg of body weight, either intramuscularly, subcutaneously, intravenously or topically.

When the BN-200 substance was compared with known antibiotics, none of the known antibiotics correspond with the present substance with respect to the properties of the producing microorganisms, and with respect to the physical and chemical properties and antimicrobial activity. Eumycetin and melinacidin as well as the BN-200 substance of the present invention have an absorption maximum at about 300 nm in methanol solution. However, Eumycetin is a cell component and the antimicrobial spectrum of Eumycetin differs from that of the BN-200 substance, Melinacidin differs from the BN-200 substance in regard to specific rotatory power. Accordingly, the BN-200 substance of the invention has been determined to be a novel substance.

The following Examples are given to illustrate the process for producing BN-200 substance in greater detail. However, the invention is not to be construed as being limited to these Examples, and needless to say, many other modifications can be used.

EXAMPLE 1

100 ml of a liquid culture medium of 2% glycerol, 1.5% peptone, 1.0% meat extract, 0.3% KCl and 0.3% $CaCO_3$ was placed into each of 25 Sakaguchi flasks (500 ml), and the flasks were each sealed with a cotton plug. Each of the flasks and its contents was sterilized at 120° C. under pressure for 10 minutes. Each culture medium was inoculated with a platinum loopful of a slant culture of Erwinia sp. BN-200 (FERM-P 3561), and cultivation was conducted with shaking at 28° C. for 20 hours. Thus, 2.4 liters of a culture broth having a potency of 20 mcg/ml was obtained.

The bacterial cells were removed by centrifugal separation at a rotation of 10,000. The supernatant liquid was passed through a column filled with 200 ml of Diaion HP-20 (a product of Mitsubishi Chemical Industries, Ltd.) for adsorption of the active ingredient. The column was thoroughly washed with water, further washed with acidic 50% aqueous methanol solution (adjusted to a pH of 2 with 6 N HCl), and eluted with alkaline 80% aqueous methanol solution (adjusted to a pH of 9 with 6 N NaOH) to extract the active ingredient. Fractions having an antimicrobial activity were collected, neutralized with 6 N hydrochloric acid, and concentrated under reduced pressure to 200 ml. The concentrate was adjusted to pH 2.0 with 1 N hydrochloric acid, and extracted with 200 ml of benzene. The extract was washed with water, dried over anhydrous sodium sulfate, and concentrated under reduced pressure to obtain a syrupy product. The syrupy product was then passed through a column (30 mm $\phi \times 800$ mm) of Sephadex LH-20 (500 ml) equilibrated with methanol, and developed with methanol (500ml) to perform gel filtration and thereby 17 to 24 active fractions (20 ml in each fraction) were obtained.

Fractions having an antimicrobial activity were collected, and concentrated under reduced pressure to dryness to obtain 12 mg of BN-200 substance as a white powder.

EXAMPLE 2

A 30-liter fermentation tank was charged with 20 liters of a culture medium containing 2% glycerol and 3% bouillon powder, and sterilized at 120° C. for 15 minites, and cooled. The culture medium in the fermentation tank was inoculated with Erwinia sp. BN-200 (FERM-P 3561) pre-cultivated for 20 hours in a Sakaguchi flask containing the same culture medium as described above, and cultivation was conducted with stirring and aeration at 28° C. and a stirring rate of 200 rpm for 8 hours at an air flow rate of 20 liters/min. Thus, 18 liters of a culture broth having a potency of 10 mcg/ml was obtained.

To the culture broth was added 1.5 liters of Diaion HP-20 as an adsorbent resin, and the batch was stirred for 15 minutes for adsorption of the active ingredient. After the adsorption, the Diaion HP-20 was removed, the resin having the active ingredient adsorbed thereon was sufficiently washed with water, washed with a 50% aqueous methanol solution adjusted to a pH of 2 with 6 N HCl, and then eluted with a 70% aqueous methanol solution adjusted to a pH of 9.0 with 6 N NaOH.

Fractions showing antimicrobial activity were collected, and neutralized to a pH of 7 with 6 N hydrochloric acid. The neutralized liquid was concentrated to 1 liter under reduced pressure, adjusted to a pH of 2.0 with 1 N hydrochloric acid, and extracted with 1 liter of ethyl acetate. The extract was washed with water, and dried. The ethyl acetate was distilled off to obtain a syrupy product. The syrup was then dissolved in methanol (10 ml), and the solution was passed through a column (30 mm $\phi \times 800$ mm) of Sephadex LH-20 (500 ml) equilibrated with methanol and developed with methanol (500ml) to obtain 17 to 24 active fractions (20 ml in each fraction). Fractions having an antimicrobial activity were collected, and concentrated under reduced pressure to dryness to obtain 70 mg of BN-200 substance as a white powder.

While the invention has been described in detail and with reference to specific embodiments thereof, it will be apparent to one skilled in the art that various changes and modifications can be made therein without departing from the spirit and scope thereof.

What is claimed is:

1. An antibiotic BN-200 substance having the following properties:
   Form and Color: white powder
   Elemental Analysis: C 67.46%, H 7.24%, N 7.55%, O 17.75% (balance);
   Molecular Weight: 520; determined from the titration value;
   Melting Point: Begins to turn brown at 150° C., and begins to decompose at 156° C.;
   Specific Rotatory Power: $[\alpha]_D^{20} = -70.7$ (C=1, methanol);
   Ultraviolet Absorption Spectrum (in methanol): as shown in FIG. 1;
   Infrared Absorption Spectrum (KBr tablet); as shown in FIG. 2;
   Solubility in Solvents: Soluble in methanol, ethanol, pyridine, dimethylformamide, acetone, and dimethyl sulfoxide, and insoluble in benzene, ethyl acetate, chloroform, carbon tetrachloride, petroleum ether, and water;
   Color Reactions: positive with ferric chloride, potassium permanganate and iodine, and negative with ninhydrin, Sakaguchi, biuret, Fehling, Molisch, and anthrone.
   Rf Values in Silica Gel Thin-Layer Chromatography:
   Chloroform-Methanol (9:1)—0.57
   Benzene-Ethanol (9:1)—0.47
   Benzene-Acetone (1:1)—0.76

2. A process for producing the antibiotic BN-200 substance of claim 1, which comprises
   aerobically cultivating Erwinia sp. BN-200 strain (FERM-P 3561/ATCC-31420), as a BN-200 substance-producing strain, in a culture medium containing assimilable carbon and nitrogen sources at a temperature of about 20° to about 35° C., and recovering the BN-200 substance from the culture broth.

* * * * *